US010429325B2

(12) United States Patent
Ito et al.

(10) Patent No.: US 10,429,325 B2
(45) Date of Patent: Oct. 1, 2019

(54) X-RAY SMALL ANGLE OPTICAL SYSTEM (71) Applicant: Rigaku Corporation, Akishima-shi, Tokyo (JP)

(72) Inventors: Kazuki Ito, Akishima (JP); Kazuhiko Omote, Akiruno (JP); Licai Jiang, Rochester Hills, MI (US)

(73) Assignee: RIGAKU CORPORATION, Akishima-Shi, Tokyo (JP)

( * ) Notice: Subject to any disclaimer, the term of this patent is extended or adjusted under 35 U.S.C. 154(b) by 183 days.

(21) Appl. No.: 15/259,581

(22) Filed: Sep. 8, 2016

(65) Prior Publication Data
US 2017/0074809 A1    Mar. 16, 2017

(30) Foreign Application Priority Data
Sep. 11, 2015  (JP) .................. 2015-179651

(51) Int. Cl.
G01N 23/201    (2018.01)
(52) U.S. Cl.
CPC ..... G01N 23/201 (2013.01); *G01N 2223/054* (2013.01)
(58) Field of Classification Search
CPC .... A61K 38/16; A61K 38/164; A61K 38/168; A61K 38/177; A61K 41/00; A61K 41/0057; A61K 48/00; A61K 48/0075; A61K 8/39; A61K 2800/43; A61K 8/0295; A61K 8/19; A61K 8/86; A61K 2800/596; A61K 31/497; A61K 8/375; A61K 2800/524; G01N 2223/054; G01N 23/201; G01N 2223/6116; G01N 23/20; G01N 2223/308; G01N 23/205; G01N 23/207; G01N 23/20008; G03F 7/70625; G21K 1/062; G21K 1/067; G21K 2201/064; G21K 1/06; G21K 2201/067; G02B 3/0012; G02B 3/0025; G02B 3/005; G02B 3/0056; G02B 5/0891; G02B 5/10
USPC .................. 378/70, 79, 84, 86, 87
See application file for complete search history.

(56) References Cited

U.S. PATENT DOCUMENTS

| | | | |
|---|---|---|---|
| 6,069,934 A * | 5/2000 | Verman ........... | G01N 23/20016 378/73 |
| 6,504,902 B2 | 1/2003 | Iwasaki et al. | |
| 7,242,746 B2 * | 7/2007 | Michaelsen ............. | G21K 1/06 250/505.1 |
| 7,439,492 B1 * | 10/2008 | Ice ......................... | B82Y 10/00 250/251 |

(Continued)

FOREIGN PATENT DOCUMENTS

WO    2013108876 A1    7/2013

*Primary Examiner* — Irakli Kiknadze
(74) *Attorney, Agent, or Firm* — Cantor Colburn LLP (57) ABSTRACT

Provided is an X-ray small angle optical system, which easily achieves a desired angular resolution, including: an X-ray source having a microfocus; a multilayer mirror having an elliptical reflection surface, and being configured to collect X-rays emitted from the X-ray source and to irradiate a sample; and an X-ray detector configured to detect scattered X-rays generated from the sample, in which the elliptical reflection surface of the multilayer mirror has a focal point A and a focal point B, in which the X-ray source is arranged such that the microfocus includes the focal point A, and in which the X-ray detector is arranged on the multilayer mirror side of the focal point B.

10 Claims, 5 Drawing Sheets

(56) References Cited

U.S. PATENT DOCUMENTS

| | | | | |
|---|---|---|---|---|
| 2004/0190681 A1* | 9/2004 | Omote | ............... | G01N 23/20 |
| | | | | 378/71 |
| 2006/0239405 A1* | 10/2006 | Verman | ............... | B82Y 10/00 |
| | | | | 378/85 |
| 2011/0268252 A1* | 11/2011 | Ozawa | ............... | G21K 1/06 |
| | | | | 378/82 |

* cited by examiner

X-RAY SMALL ANGLE OPTICAL SYSTEM

CROSS-REFERENCE TO RELATED APPLICATION

The present application claims priority from Japanese application JP 2015-179651, filed on Sep. 11, 2015, the content of which is hereby incorporated by reference into this application.

BACKGROUND OF THE INVENTION

Field of the Invention

The present invention relates to an X-ray small angle optical system.

Description of the Related Art

Figure 1:
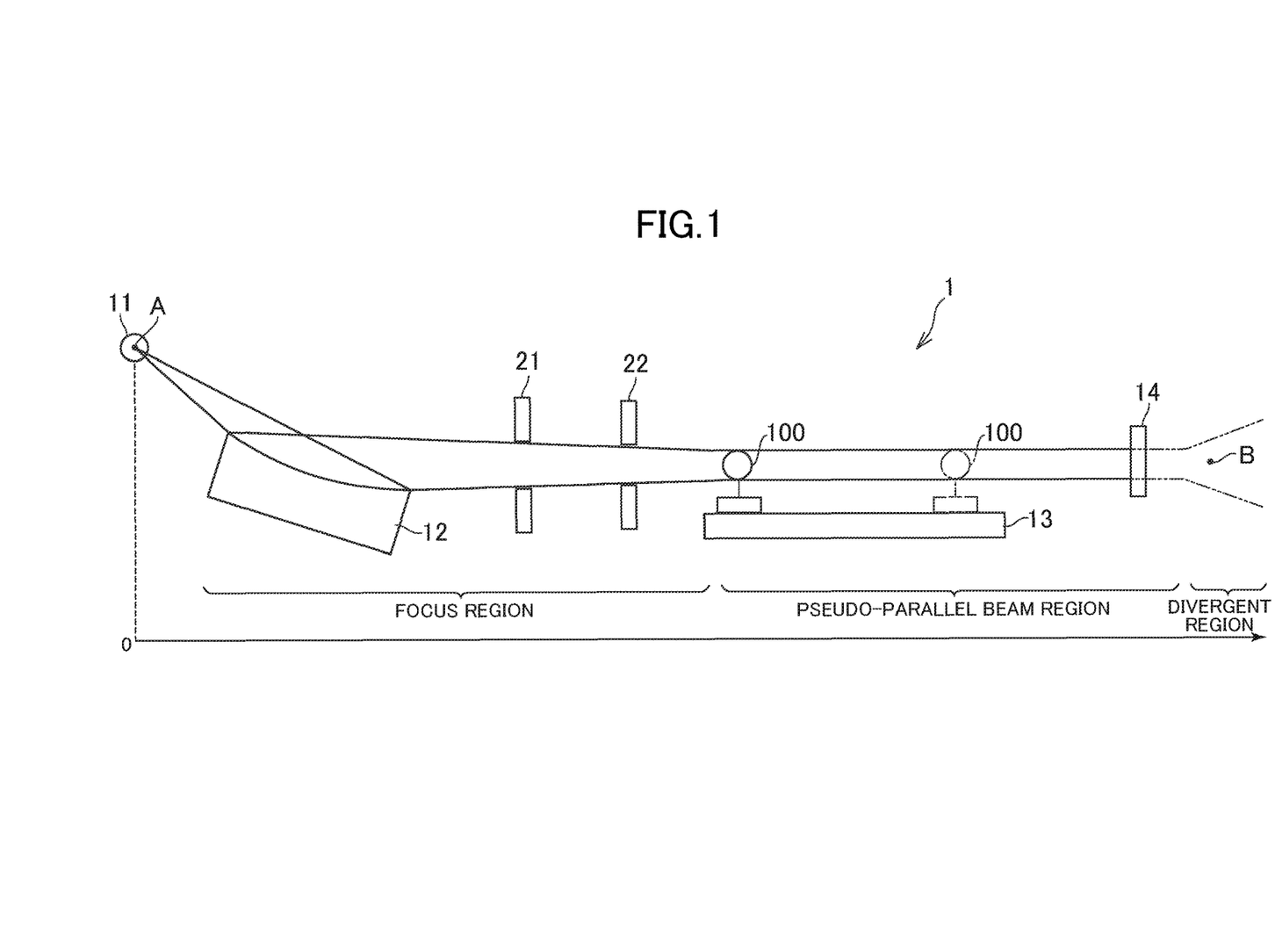
FIG. 1 is a schematic view for illustrating the structure of an X-ray small angle optical system according to an embodiment of the present invention.

There has been used an X-ray small angle optical system, which is configured to collect X-rays emitted from an X-ray source by a focusing device. In U.S. Pa. No. 6,504,902, there is disclosed an X-ray optical device including a multilayer mirror having elliptical reflection surfaces. As illustrated in FIG. 1 of U.S. Pat. No. 6,504,902, a sample S is placed at a convergent point (focal point B) of X-rays reflected from a multilayer mirror 1, and an X-ray detector 3 is arranged downstream thereof. In other words, a region from the focusing device (multilayer mirror 1) to the sample is a focus region, and the sample is placed at a focal position of the focusing device. The X-ray detector is arranged in a divergent region, which is further downstream of the focal position.

In an X-ray small angle optical system, which uses emitted light X-rays from an electron synchrotron, a high-brightness and low-divergence (highly directional) X-ray source may be achieved. Therefore, in an X-ray small angle optical system including such X-ray source and a focusing device configured to monochromatize wavelengths, an X-ray detector is arranged at a focal position, and a sample is placed in a focus region between the focusing device and the focal position, to thereby optimize a small angular resolution.

SUMMARY OF THE INVENTION

In an X-ray small angle optical system, it is required to separate X-rays that have entered and transmitted through or reflected from a sample, from scattered X-rays from the sample, with as small a scattering angle as possible. In other words, a high small angular resolution, with which the scattered X-rays may be observed or measured under such condition, is required, and it is required to achieve the high small angular resolution in designing the X-ray small angle optical system. The "high small angular resolution" as used herein refers to a case where a scattering angle $2\theta$ is less than $0.1°$, for example.

In the X-ray optical device disclosed in U.S. Pat. No. 6,504,902, the sample S is fixed at the convergent point (focal point B). When a distance between the sample S and the X-ray detector 3 is increased, air scattering of the X-rays is increased, and a background rises. As a result, an S/N ratio may become worse. Therefore, there is a description that it is desired to cover a gap between the sample S and the X-ray detector 3 with a vacuum pass. The sample S may be fixed at the convergent point to achieve a strong flux of the X-rays at a position of the sample, and the X-ray detector 3 may be moved to obtain a desired small angular resolution. However, there arise problems in that, when the gap between the sample S and the X-ray detector 3 is to be covered with the vacuum pass, the movement has its limitation, and when the detector becomes large, the detector becomes difficult to implement.

In recent years, with improvements in processing technologies for focusing devices, focusing devices having a long focal lengths have been achieved. Moreover, processing technologies for controlling mosaicities of focusing devices have been improved. The "mosaicity" as used herein is a conceptual indicator indicating a degree of orientation of a crystal forming a focusing device. When the crystal of the focusing device is irradiated with X-rays from a light source having a sufficiently small light source size, a sharp focal point is ideally obtained, but in reality, a finite-size focal point having a width is observed. This width results from the finiteness of the light source size and imperfection in the crystal. A multilayer mirror having an elliptical reflection surface is an artificial crystal obtained by alternately and repetitively laminating heavy element layers and light element layers. With improvements in processing technologies for multilayer mirrors, a processing accuracy of controlling a mosaicity of the artificial crystal has been improved.

It has been known that, in an X-ray small angle optical system including an X-ray source having a relatively large microfocus, and a mosaic crystal monochromator as a focusing device, there is a pseudo-focus region between the focusing device and the focal position. In the pseudo-focus region, a width of a light flux of X-rays is changed gently. With the width of the light flux of the X-rays being changed gently, the pseudo-focus region may also be referred to as a "pseudo-parallel beam region".

The inventors of the present invention have conducted an extensive study on a multilayer mirror having an elliptical reflection surface. As a result, the inventors have found that, when such multilayer mirror is used as a focusing device, an X-ray source, which is currently in practical use, may be used to achieve a pseudo-parallel beam region between the multilayer mirror and a focal position.

The present invention has been made based on such finding, and therefore has an object to provide an X-ray small angle optical system, which easily achieves a desired angular resolution.

(1) In order to solve the above-mentioned problem, according to one embodiment of the present invention, there is provided an X-ray small angle optical system, including: an X-ray source having a microfocus; a multilayer mirror having an elliptical reflection surface, and being configured to collect X-rays emitted from the X-ray source and to irradiate a sample; and an X-ray detector configured to detect scattered X-rays generated from the sample, in which the elliptical reflection surface of the multilayer mirror has a focal point A and a focal point B, in which the X-ray source is arranged such that the microfocus includes the focal point A, and in which the X-ray detector is arranged on the multilayer mirror side of the focal point B, that is, the X-ray detector is arranged closer to the multilayer mirror than the focal point B.

(2) In the X-ray small angle optical system according to Item (1), the multilayer mirror may have a mosaicity such that a pseudo-parallel beam region is formed between the multilayer mirror and the focal point B.

(3) The X-ray small angle optical system according to Item (2) may further include a sample stage configured to support the sample in the pseudo-parallel beam region, and to move the sample along an optical axis direction of the X-rays in the pseudo-parallel beam region.

(4) In the X-ray small angle optical system according to Item (2) or (3), the pseudo-parallel beam region may be a region including a position at which a beam size of an X-ray beam has a minimum value, in which the beam size is 1.2 times the minimum value or less.

(5) In the X-ray small angle optical system according to any one of Items (1) to (4), a distance between a center position of the elliptical reflection surface of the multilayer mirror and the focal point B may be 1,000 mm or more.

According to the present invention, an X-ray small angle optical system which easily achieves a desired angular resolution is provided.

DETAILED DESCRIPTION OF THE INVENTION

Now, an embodiment of the present invention is described referring to the drawings. For clearer illustration, some sizes, shapes, and the like are schematically illustrated in the drawings in comparison to actual ones. However, the sizes, the shapes, and the like are merely an example, and do not limit understanding of the present invention. Further, like elements as those described relating to the drawings already referred to are denoted by like reference symbols herein and in each of the drawings, and detailed description thereof is sometimes omitted as appropriate.

FIG. 1 is a schematic view for illustrating the structure of an X-ray small angle optical system 1 according to an embodiment of the present invention. The X-ray small angle optical system 1 according to this embodiment is an X-ray small angle scattering device used on a laboratory basis (that is, in a laboratory) for example. The X-ray small angle optical system 1 includes an X-ray source 11, a multilayer mirror 12, a sample stage 13 configured to support a sample 100, and an X-ray detector 14.

The X-ray source 11 is an X-ray generator having a microfocus (minute light source size), and has a rotor target containing copper (Cu) as a target material. X-ray generation regions on side surfaces of the rotor target are linear (flat ellipsoidal). However, the X-rays are extracted in an oblique direction with respect to a major axis, and hence an effective focal point size (light source size) is a microfocus with a diameter of 0.07 mm. An output is 1.2 kW. Moreover, an applied voltage is 40 kV, and an applied electric current is 30 mA.

The multilayer mirror 12 has an elliptical reflection surface. The elliptical reflection surface of the multilayer mirror 12 has a focal point A and a focal point B, and the X-ray source 11 is arranged such that the microfocus includes the focal point A. The focal length is 4,000 mm, and a length of the mirror is 80 mm. The "focal length" as used herein refers to a distance from a center position of the elliptical reflection surface of the multilayer mirror 12 to the focal point B.

An artificial crystal of the multilayer mirror 12 has a desired mosaicity, and in relation to a finite size of the microfocus of the X-ray source 11, as illustrated in the figure, X-rays reflected from the multilayer mirror 12 form, in order from the multilayer mirror 12 to the focal point B, a focus region and a pseudo-parallel beam region. Moreover, the reflected X-rays form a divergent region near the focal point B and further downstream thereof. In other words, the pseudo-parallel beam region is formed between the multilayer mirror 12 and the focal point B. The sample 100 and X-ray detector 14 are placed in the pseudo-parallel beam region, and hence even when the sample 100 is moved along an optical axis direction of the X-rays in the pseudo-parallel beam region, a change in light flux of the X-rays, with which to irradiate the sample 100, is suppressed. As a result, the sample 100 may be effectively irradiated with the X-rays from the multilayer mirror 12 (that is, the light flux of the X-rays to irradiate the sample 100 is increased).

The sample stage 13 may support the sample 100 in the pseudo-parallel beam region. Further, the sample stage 13 has a movement mechanism, and may move the sample 100 along the optical axis direction of the X-rays (that is, in a right and left direction in the figure) in the pseudo-parallel beam region. When the sample 100 is brought closer to the multilayer mirror 12, a small angular resolution (detectable minimum angle) is improved, and when the sample 100 is brought closer to the focal point B, a measurement range may be increased.

Figure 2:
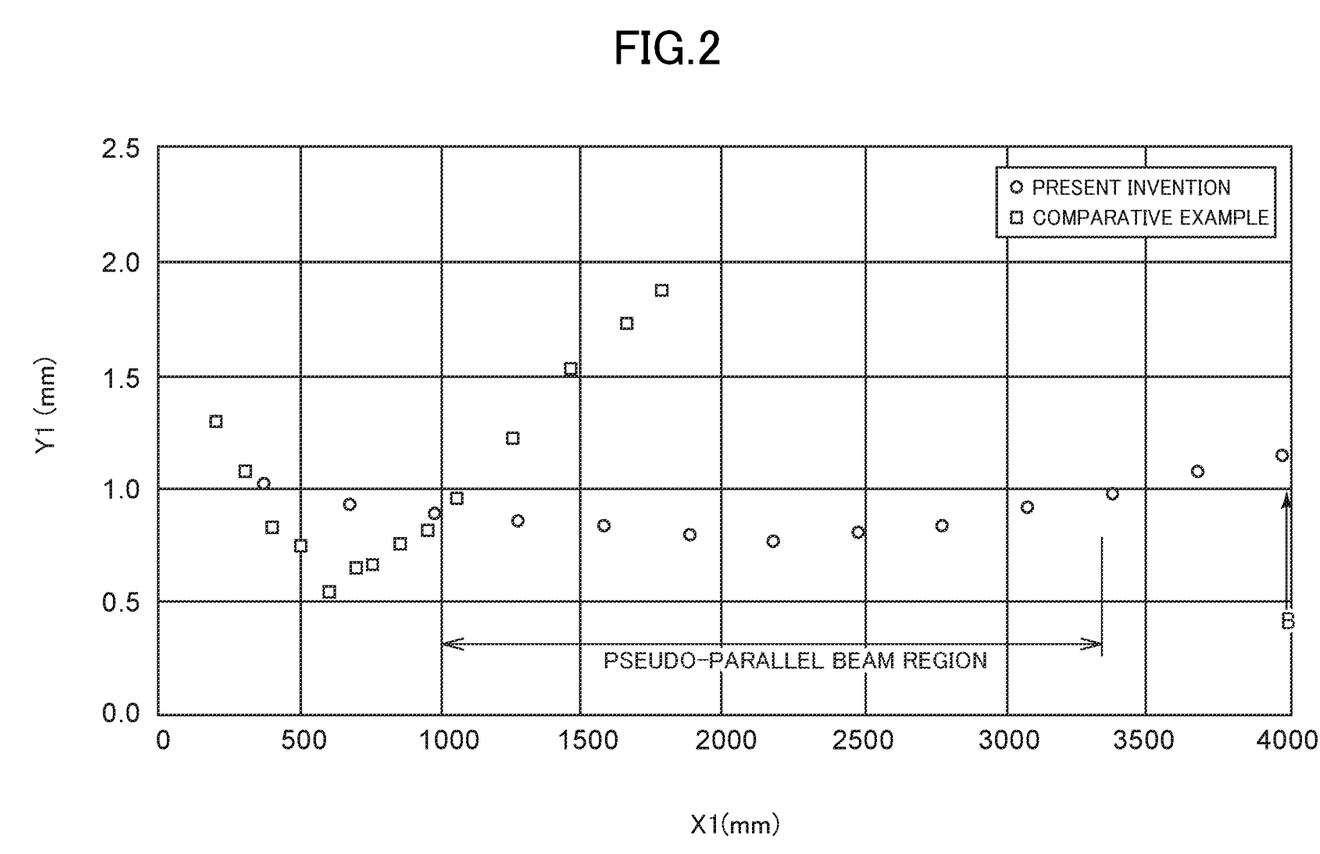
FIG. 2 is a graph for showing a result of measuring an X-ray beam from a multilayer mirror according to the embodiment of the present invention.

FIG. 2 is a graph for showing a result of measuring an X-ray beam from the multilayer mirror 12 according to this embodiment. In the figure, a relationship between a beam size Y1 (mm) of the X-ray beam and a distance X1 (mm) from the X-ray source 11 is shown. The multilayer mirror 12 according to this embodiment is indicated by the symbol "○", and a multilayer mirror according to a comparative example is indicated by the symbol "□". With the finite size of the microfocus of the X-ray source 11 according to this embodiment, and the mosaicity of the multilayer mirror 12 according to this embodiment, as shown in the figure, the beam size of the X-ray beam is changed very gently. The beam size of the X-ray beam is defined here by a full width at half maximum (FWHM).

Here, the pseudo-parallel beam region is defined by the beam size of the X-ray beam. When $x1=2,200$, the beam size of the X-ray beam has the minimum value of 0.8. When the pseudo-parallel beam region is defined to be a region in which the beam size is 1.2 times the minimum value or less, the pseudo-parallel beam region is a range in which x is 1,000 mm to 3,300 mm. With the X-ray small angle optical system 1 according to this embodiment, the focal length is as long as 4,000 mm, and the range of the pseudo-parallel beam region may achieve a wide range of 2,300 mm. In such region, the sample 100 may be placed on the sample stage 13.

Meanwhile, with the multilayer mirror according to the comparative example, the focal length is short, and the beam size of the X-ray beam is changed abruptly, with the result that the pseudo-parallel beam region cannot be secured. The multilayer mirror 12 according to this embodiment is achieved by the long focal length and the improved processing accuracy of the desired mosaicity.

Figure 3:
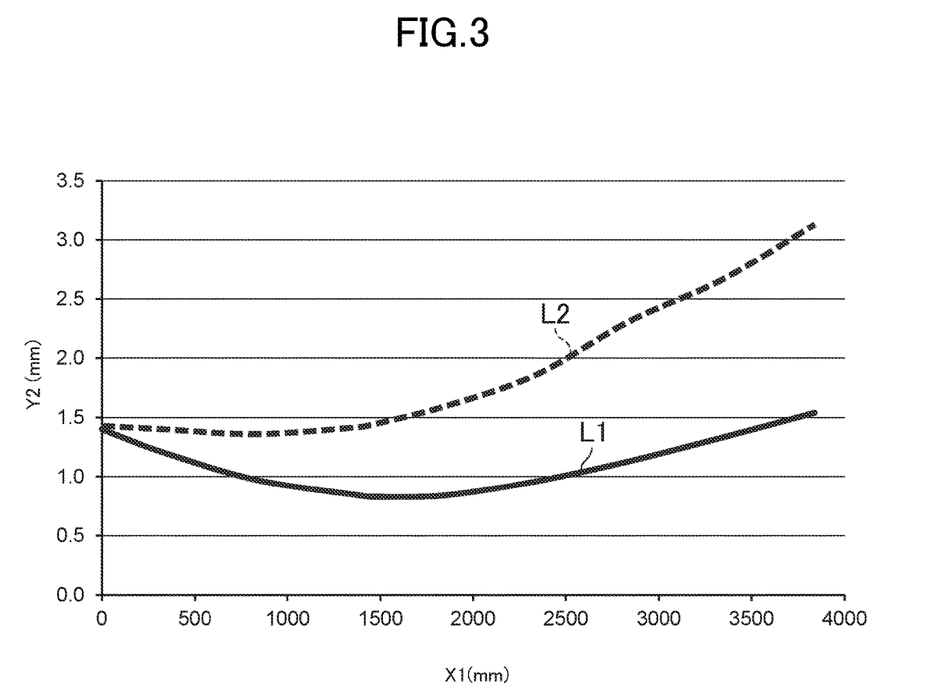
FIG. 3 is a graph for showing a result of calculating a beam width of the X-ray beam from the multilayer mirror according to the embodiment of the present invention.

FIG. 3 is a graph for showing a result of calculating the beam width of the X-ray beam of the multilayer mirror 12 according to this embodiment. The vertical axis Y2 (mm) in the figure indicates the beam width of the X-ray beam. The horizontal axis X1 (mm) in the figure indicates a distance from (the center position of the reflection surface of) the multilayer mirror 12. In the figure, the full width at half maximum (FWHM: beam size) is indicated by the solid line L1, and a width that is 10% of the maximum value is indicated by the broken line L2. Not only in the measurement result shown in FIG. 2, but also in the calculation result, it can be seen that the beam width of the X-ray beam is changed gently.

Figure 4A:
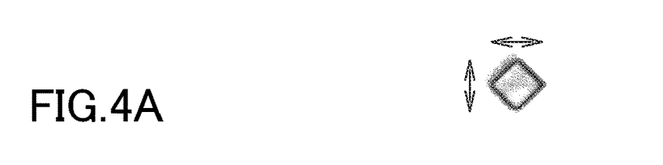
FIG. 4A is a view for illustrating a cross section of the X-ray beam from the multilayer mirror according to the embodiment of the present invention.
Figure 4B:
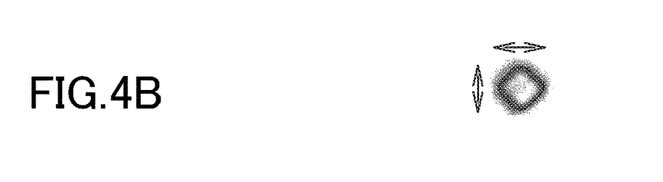
FIG. 4B is a view for illustrating a cross section of the X-ray beam from the multilayer mirror according to the embodiment of the present invention.
Figure 4C:
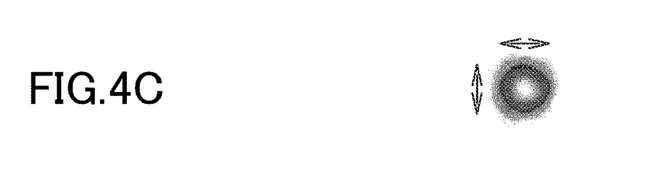
FIG. 4C is a view for illustrating a cross section of the X-ray beam from the multilayer mirror according to the embodiment of the present invention.
Figure 4D:
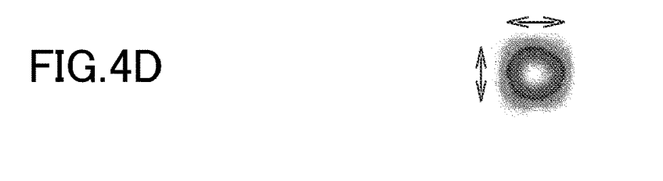
FIG. 4D is a view for illustrating a cross section of the X-ray beam from the multilayer mirror according to the embodiment of the present invention.
Figure 4E:
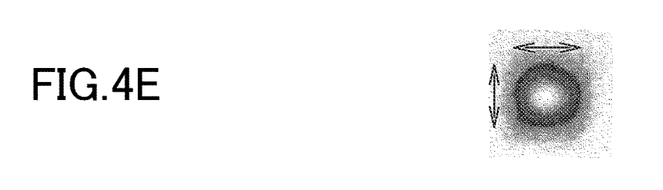
FIG. 4E is a view for illustrating a cross section of the X-ray beam from the multilayer mirror according to the embodiment of the present invention.
Figure 4F:
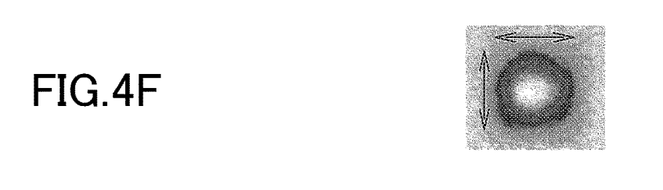
FIG. 4F is a view for illustrating a cross section of the X-ray beam from the multilayer mirror according to the embodiment of the present invention.

FIGS. 4A to 4F are views for illustrating cross sections of the X-ray beam from the multilayer mirror 12 according to this embodiment. In the views illustrated in FIG. 4A to FIG. 4F, measured intensities of the X-ray beam on planes perpendicular to an optical axis are schematically illustrated. In FIG. 4A to FIG. 4F, there are illustrated the cross sections of the X-ray beam at positions at which distances from the multilayer mirror 12 are 171 mm, 1,071 mm, 1,971 mm, 2,571 mm, 3,171 mm, and 3,771 mm in the stated order, respectively. As described above, the beam size of the X-ray beam is defined by the full width at half maximum (FWHM). However, an actual shape of the cross section of the X-ray beam may not necessarily be circular. In this embodiment, too, as illustrated in FIG. 4A, the shape is substantially square in the vicinity of the multilayer mirror 12. Also in such case, the measured intensity of the X-ray beam is orthogonally projected in each of a horizontal direction (first direction) and a vertical direction (second direction), which is perpendicular to the horizontal direction, and the full width at half maximum is determined in each direction. Then, an average value of the full widths at half maximum may be set as the beam size. The thus obtained beam size is shown in FIG. 2.

Figure 5:
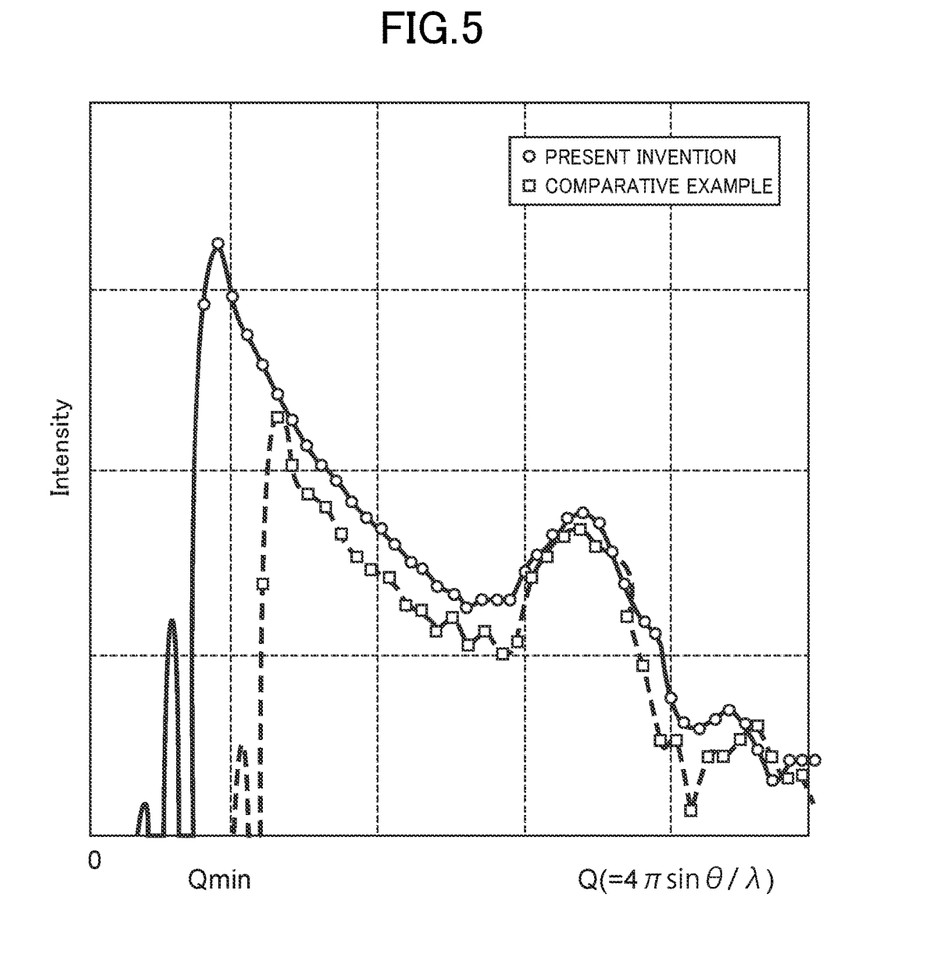
FIG. 5 is a graph for showing a result of measuring scattered X-rays from a sample in the X-ray small angle optical system according to the embodiment of the present invention.

FIG. 5 is a graph for showing a result of measuring scattered X-rays from the sample 100 in the X-ray small angle optical system 1 according to this embodiment. In the figure, a relationship between an intensity of the scattered X-rays and an absolute value Q of a scattering vector is shown. As in FIG. 2, measurement results according to this embodiment of the present invention are indicated by the symbol "○", and the measurement results according to a comparative example are indicated by the symbol "□". The scattering vector Q shown on the horizontal axis of the figure is defined as: $Q=4\pi \sin \theta/\lambda$, where $\theta$ is a scattering angle. As shown in the figure, the measurable minimum value Qmin of the scattering vector Q indicates a small angular resolution, and as Qmin becomes smaller, the small angular resolution becomes higher. Qmin in this embodiment is smaller than in the comparative example, and a significant effect of the present invention is obtained.

In the measurement shown in FIG. 5, in both of this embodiment and the comparative example, the distance between the sample and the X-ray detector is 1,300 mm. In the comparative example, as in U.S. Pat. No. 6,504,902, the sample is placed at the focal position of the multilayer mirror.

The X-ray small angle optical system 1 according to this embodiment has been described above. With the X-ray small angle optical system 1 according to this embodiment, which is a collecting optical system, a desired small angular resolution can be obtained. The region in which the sample 100 is placed is the pseudo-parallel beam region, and hence a variation in irradiation amount (irradiation area) of the X-rays to irradiate the sample 100, which is changed with the movement of the sample 100, can be suppressed, and the irradiation amount of the X-rays to irradiate the sample 100 can be increased.

The X-ray small angle optical system 1 according to this embodiment may include any optical system, such as a two-pinhole optical system, a three-pinhole optical system, or a Kratky optical system, and may be widely applied to an optical system using a two-dimensional small-angle X-ray scattering (SAXS). In FIG. 1, an example of the two-pinhole optical system is illustrated, and two pinhole slits 21 and 22 are included. The X-ray small angle optical system 1 according to this embodiment is optimal for small angle scattering measurement, but may be applied to a general X-ray diffractometer, a general scattering measurement device, and especially the one that requires low angle measurement. Moreover, it is desired that, with the multilayer mirror 12 of the X-ray small angle optical system 1 according to this embodiment, the distance between the center position of the elliptical reflection surface of the multilayer mirror 12 and the focal point B be 1,000 mm or more. It is more desired that the distance be 2,000 mm or more. It is further desired that the distance be 3,000 mm or more. With the achievement of the multilayer mirror 12 having the long focal length, a large space can be secured between the multilayer mirror 12 and the focal point B, and the sample 100 may be placed in such region. Further, a curvature radius of the reflection surface of the multilayer mirror 12 having such long focal length is long. However, even with such reflection surface, the technology of controlling the mosaicity has been improved, and hence such region can be used as the pseudo-parallel beam region.

While there have been described what are at present considered to be certain embodiments of the invention, it will be understood that various modifications may be made thereto, and it is intended that the appended claims cover all such modifications as fall within the true spirit and scope of the invention.

What is claimed is:

1. An X-ray small angle optical system for use with a sample, comprising:
   an X-ray source having a microfocus;
   a multilayer mirror having an elliptical reflection surface, and being configured to collect X-rays emitted from the X-ray source and to irradiate the sample;
   a sample stage configured to support the sample; and
   an X-ray detector configured to detect scattered X-rays generated from the sample,
   wherein the elliptical reflection surface of the multilayer mirror has a focal point A and a focal point B which are determined by a shape of the elliptical reflection surface, wherein the X-ray source is arranged such that the microfocus includes the focal point A, and wherein the X-ray detector is interposed between the sample stage and the focal point B.

2. The X-ray small angle optical system according to claim 1, wherein the multilayer mirror has a mosaicity structured to form a pseudo-parallel beam region, where a width of the X-ray is changed gently between the multilayer mirror and the focal point B.

3. The X-ray small angle optical system according to claim 2, wherein the sample stage supports the sample in the pseudo-parallel beam region, and moves the sample along an optical axis direction of the X-rays in the pseudo-parallel beam region.

4. The X-ray small angle optical system according to claim 2, wherein the pseudo-parallel beam region is a region including a position at which a beam size of an X-ray beam has a minimum value, in which the beam size is 1.2 times the minimum value or less.

5. The X-ray small angle optical system according to claim 3, wherein the pseudo-parallel beam region is a region including a position at which a beam size of an X-ray beam has a minimum value, in which the beam size is 1.2 times the minimum value or less.

6. The X-ray small angle optical system according to claim 1, wherein a distance between a center position of the elliptical reflection surface of the multilayer mirror and the focal point B is 1,000 mm or more.

7. The X-ray small angle optical system according to claim 2, wherein a distance between a center position of the elliptical reflection surface of the multilayer mirror and the focal point B is 1,000 mm or more.

8. The X-ray small angle optical system according to claim 3, wherein a distance between a center position of the elliptical reflection surface of the multilayer mirror and the focal point B is 1,000 mm or more.

9. The X-ray small angle optical system according to claim 4, wherein a distance between a center position of the elliptical reflection surface of the multilayer mirror and the focal point B is 1,000 mm or more.

10. The X-ray small angle optical system according to claim 5, wherein a distance between a center position of the elliptical reflection surface of the multilayer mirror and the focal point B is 1,000 mm or more.

* * * * *